United States Patent [19]

Miwa et al.

[11] Patent Number: 4,822,738
[45] Date of Patent: Apr. 18, 1989

[54] TRANSDUCIBLE COMPOSITE PLASMID

[75] Inventors: Kiyoshi Miwa, Matsudo; Konosuke Sano, Tokyo, both of Japan

[73] Assignee: Ajinomoto Co., Inc., Tokyo, Japan

[21] Appl. No.: 135,481

[22] Filed: Dec. 21, 1987

Related U.S. Application Data

[63] Continuation of Ser. No. 719,951, Apr. 4, 1985, abandoned.

[30] Foreign Application Priority Data

Apr. 4, 1984 [JP] Japan ................................ 59-66879
Oct. 5, 1984 [JP] Japan ............................... 59-209060

[51] Int. Cl.$^4$ ..................... C12N 1/20; C12N 15/00; C12P 21/00; C12R 1/15
[52] U.S. Cl. ................................ 435/252.3; 435/68; 435/172.1; 435/172.3; 435/320; 435/843; 935/26; 935/27; 935/29; 935/31; 935/72
[58] Field of Search ...................... 435/68, 70, 71, 91, 435/172.1, 172.2, 172.3, 235, 236, 253, 320, 840, 843, 844, 845; 935/26, 27, 29, 31, 72

[56] References Cited

PUBLICATIONS

Miwa et al., x Gene 39: 281 (1985).
"On the Transducing Phages in Glutamic Acid-Producing Bacteria" Haruo Momose et al.; J. Gen. Appln. Micriobiol., 22, 119–129 (1976).
"Development of Cosmid Vector of Brevibacterium"; Kiyoshi Miwa et al.; Annual Meeting of the Japanese Society of Biochemistry at Tokyo (1984).
"Development of Host/Vector System of *Brevibacterium lactofermentum*;" Annual Meeting of the Society of Fermentation Technology, Japan at Osaka (1983).
"Molecular Cloning of Homoserine Dehydrogenase (HD) Gene of *Brevibacterium Lactofermentum* and Overproduction of Threonine" Masaaki Ishida et al.; Annual Meeting of the Society of Ferment. Technology, Japan at Osaka (1983).
"Molecular Cloning of Phosphoenolpyruvate Carboxylase Gene of *Brevivacterium Lactofermentum*"; Koichi Ito et al.; Annual Meeting of the Agricultural Chemical Society of Japan, (1984).

*Primary Examiner*—James Martinell
*Attorney, Agent, or Firm*—Oblon, Fisher, Spivak, McClelland & Maier

[57] ABSTRACT

A composite vector capable of the transduction of a Coryneform bacterium, which comprises a first DNA segment containing at least the genetic information for replication from a plasmid capable of propagating in a Coryneform bacterium and a second DNA segment containing at least a DNA region of a phage capable of propagating in the Coryneform bacterium, wherein the DNA region is incorporated into a particle of the aforementioned phage when the aforementioned bacterium is infected with the phage, is disclosed.

11 Claims, 1 Drawing Sheet

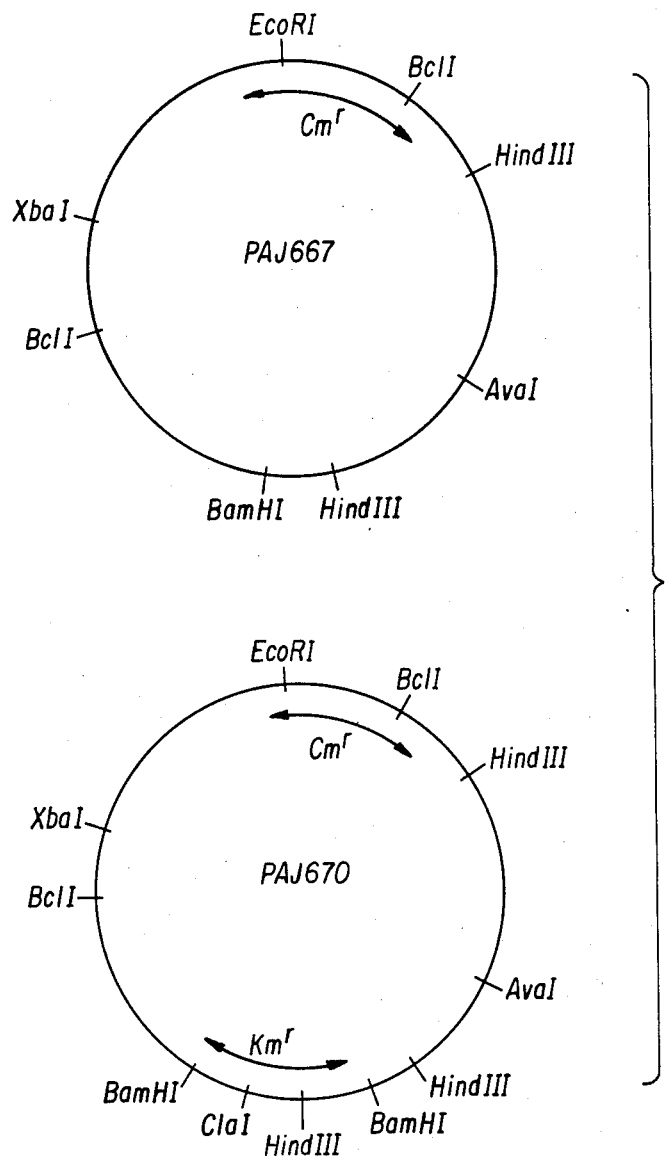

TRANSDUCIBLE COMPOSITE PLASMID

This application is a continuation of application Ser. No. 719,951, filed on Apr. 4, 1985, now abandoned.

BACKGROUND OF THE INVENTION

1. Field of the Invention

This invention relates to a transducible composite plasmid and more particularly to a composite plasmid capable of transduction having a Coryneform glutamicacid-producing bacterium as the host thereof.

2. Description of the Prior Art

Some species of the Coryneform glutamic-acid-producing bacteria are known to produce large amounts of L-glutamic acid, and some other species, particularly certain mutants of wild strains, produce large quantities of amino acids such as lysine and purine nucleotides such as inosinic acid. These large producers are industrially important microorganisms. Recently, attempts have been made to commercially breed and improve microorganisms using the recombinant DNA techniques. Development of recombinent DNA techniques is also now well under way with respect to Coryneform glutamic acid-producing bacteria. For example, the development of a host-vector system for Corynebacterium glutamicum, the development of a host-vector system for *Brevibacterium lactofermentum,* and the breeding of threonine-producing microorganisms are reported respectively in Glossary of Lectures at the 1983 General Meeting of Japan Agricultural Chemical Society, page 333 (1983) and Glossary of Lectures at the 1983 General Meeting of Japan Fermentation Engineering Society, page 283 and page 284 (1983). Composite plasmids disclosed in European Application No. 83302478.9 (publication no. 0093611; U.S. application Ser. No. 386,980) are also advantageous vectors for use in Coryneform glutamic-acid-producing bacteria as the hosts in recombinant DNA investigations.

The vector systems heretofore known for host Coryneform glutamic-acid-producing bacteria invariably use plasmids as their vectors. For successful insertion of these plasmid vectors into their hosts, separation of the plasmid vectors and subsequent treatment of separated plasmid vectors (by such complicated means of transformation as the protoplast method or the calcium treatment method) are indispensable.

In *Escherichia coli,* there is available the socalled cosmid, i.e., a recombined plasmid possessing a DNA region including a cohesive end (COS) originating in the lambda phage [Fukumaki, U., Shimada, I., & Takagi, Y., Proc. Natl. Acad. Sci. USA, 73, 3238 (1976) and Collins, J. Hohn, B.: Proc. Natl. Acad. Sci. USA, 75, 4242 (1978)].

This cosmid is characterized by its ability to be easily transmitted from a host strain to another strain by a transduction method using a phage. Herein, the term "transduction method" is defined as the insertion of a gene through the medium of a phage particle, as described in Protein Nucleic Acid-Enzyme, extra issue, "Experimental Methods for Microorganism and Phage Heredity," page 64 (1972). This method is based on the principle that when a cosmid-retaining strain of bacteria is infected with an intact phage, for example, there is formed a pseudo-phage particle containing cosmid DNA instead of natural intact phage DNA in a fixed proportion, and this particle acquires the ability to effect introduction of the cosmid DNA into a new host strain. When this cosmid is adopted, the desired transmission of genetic information is effected by simply preparing the phage bacteriolyzate of a donor bacterium and mixing this bacteriolyzate with a recipient bacterium, thereby causing infection. Thus, this method accomplishes the transmission of genetic information very rapidly and conveniently as compared to other methods using a plasmid.

In none of the Coryneform glutamic-acid-producing bacteria, however, is there found a vector capable of transduction. Thus, none of the known vectors permit transmissible of a plasmid by the transduction method.

SUMMARY OF THE INVENTION

Accordingly, it is an object of this invention to provide a vector capable of transduction when used with a Coryneform bacterium.

This and other objects of the invention as will hereinafter become more readily apparent have been accomplished by providing a composite plasmid capable of transducing a Coryneform bacterium, wherein said composite plasmid comprises (1) a first DNA segment containing at least the genetic information for replication of a plasmid capable of propagating within a Coryneform bacterium and (2) a second DNA segment containing at least a DNA region of a phage capable of propagating in a Coryneform bacterium, wherein said DNA region of said phage is a region incorporated into a particle of said phage when said bacterium is infected with said phage.

BRIEF DESCRIPTION OF THE DRAWING

A more complete appreciation of the invention and many of the attendant advantages thereof will be readily obtained by reference to the following detailed description when considered in connection with the accompanying drawing, wherein:

The FIGURE shows restriction maps of two plasmids: pAJ 667 and pAJ 670.

DESCRIPTION OF THE PREFERRED EMBODIMENTS

The inventors have succeeded in producing a composite plasmid capable of transduction by the combination of a plasmid having a Coryneform glutamic-acid-producing bacterium as its host with a DNA fragment of a phage having a Coryneform glutamic-acid-producing bacterium as its host. The present invention, therefore, residues in a composite vector comprising (1) a first DNA segment containing at least the genetic information for replication from a plasmid capable of propagating within the cell of a Coryneform glutamic-acid-producing bacterium and (2) a second DNA segment containing at least the DNA region of a phage capable of propagating within the cell of the aforementioned bacterium, which phage DNA region is such as to cause incorporation into the particle of the aforementioned phage when the aforementioned bacterium is infected with the phage.

This composite plasmid can be inserted very simply and rapidly into the cell of a Coryneform glutamic-acid-producing bacterium by the transduction method and therefore proves highly useful for the breeding of industrial microorganism strains by recombinant DNA methods.

Coryneform bacteria are aerobic, gram-positive rods, are non-acid-fast and are described in Bergey's Manual of Determinative Bacteriology, 8th ed., page 599 (1974).

The Coryneform glutamic-acid-producing bacteria according to the present invention include species of Coryneform bacteria capable of producing large amounts of glutamic acid and mutants derived from such species and deprived of the glutamic-acid-producing property. Examples of the wild strain are as follows:

| | |
|---|---|
| Brevibacterium divaricatum | ATCC 14020 |
| Brevibacterium saccharolyticum | ATCC 14066 |
| Brevibacterium immariophilum | ATCC 14068 |
| Brevibacterium lactofermentum | ATCC 13869 |
| Brevibacterium roseum | ATCC 13825 |
| Brevibacterium flavum | ATCC 13826 |
| Brevibacterium thiogenitalis | ATCC 19240 |
| Corynebacterium acetoacidophilum | ATCC 13870 |
| Corynebacterium acetoglutamicum | ATCC 15806 |
| Corynebacterium callunae | ATCC 15991 |
| Corynebacterium glutamicum | ATCC 13032, 13060 |
| Corynebacterium lilium | ATCC 15990 |
| Corynebacterium melassecola | ATCC 17965 |
| Microbacterium ammoniaphilum | ATCC 15354 |

The Coryneform glutamic-acid-producing bacteria include mutants deprived of the glutamic-acid-producing property and mutants capable of producing amino acids such as lysine and arginine, purine nucleosides such as inosine, purine nucleotides such as inosine-5'-monophosphate, and other substances.

The plasmid which is propagatable within the cell of such a Coryneform glutamic acid-producing bacterium can be any of the plasmids known to the art. Examples of the plasmid include pAM330, pAM286 (Japanese Laid-open Patent Application 58-67699), pHM1519 (Japanese Laid-open Patent Application 58-77895), pAJ655, pAJ611, pAJ1844 (Japanese Laid-open Patent Application 58-192900), pCG1 (Japanese Laid-open Patent Application 57-134500), pCG2 (Japanese Laid-open Patent Application 58-35197), and pCG4 and pCG11 (Japanese Laid-open Patent Application 58-183799).

The phage which is capable of propagating within the cell of a Coryneform glutamic-acid-producing bacterium can also be any of the phages known to the art. Examples of the phage include such phages as CP-2, CP-3, CP-5, and CP-7, which are described in J. Gen. Appl. Microbiol., 22, 119 (1976) and such phages as φCG1, φCG2, φCG3, φCG4, and φCG5 found in *Corynebacterium glutamicum* as the host which are described in Glossary of Lectures at the 1983 General Meeting of Japan Agricultural Chemical Society, Page 332, and "Fermentation and Industry," Vol. 35, pages 198, 294, 392, and 473 (1977).

The composite plasmid of the present invention may include the aforementioned plasmid DNA wholly as part of the composite plasmid, but it is minimally required to contain at least the genetic information for replication of the plasmid DNA. As regards the aforementioned phage, the composite plasmid of the present invention may contain the DNA of the phage wholly as part thereof, but is is minimally required to contain at least the DNA region of the phage which is necessary for incorporation of phage material into the particle of the forming phage when the Coryneform glutamic-acid-producing bacterium is infected by this intact phage. More often than not, the DNA region which is necessary for incorporation of phage material into the particle of the phage when the host is infected by that intact possesses a cohesive end (COS).

The plasmid DNA and the phage DNA can be isolated from bacterial cells by any conventional method available for the purpose. Then the phage DNA and the plasmid DNA are separately fragmented using restriction enzymes. The desired plasmid capable of transduction can be obtained by using the fragments of phage DNA wholly in unfractionated form as the starting material. Additionally, as is widely known from the reported experiment on the cosmid of *Escherichia coli* (Proc. Natl. Acad. Sci. USA, 73, 3238 (1976)), where the object is attained by the insertion into the plasmid of the DNA fragment containing the COS region of the phage, the desired recombined plasmid can be efficiently obtained by using the COS-containing fragment in an isolated form as described below. The cohesive end of the phage DNA generally forms a single-stranded complementation end. It is well known that two cohesive ends are coupled by hydrogen bonding but are easily separated by the operation of heating and quenching. By analyzing the DNA fragment by agarosegel electrophoresis before and after the procedure of heating and quenching, therefore, the DNA fragment possessing a cohesive end can be easily identified. After the DNA fragment possessing a cohesive end has been identified, this fragment can be extracted from the agarose gel used in the electrophoresis and then purified by any conventional method.

For the linkage of the phage DNA fragment so obtained and the fragmented or linearized plasmid DNA, the ordinary methods resorting to use of ligase can be adopted. Otherwise, this linkage may be attained by a procedure which comprises adding deoxyadenylic acid and deoxythymidylic acid (or deoxyguanylic acid and deoxycytidylic acid) respectively to the ends of the phage DNA fragment and the ends of the cleaved vector DNA by the use of a terminal transferase, mixing the resulting addition products, and annealing the mixture.

The introduction of the product of linkage between the phage DNA and the plasmid DNA into a recipient bacterium belonging to the Coryneform glutamic-acid-producing bacteria can be accomplished by the method of treating the cell of a recipient bacterium with calcium chloride, thereby enhancing the transmissibility of DNA, as reported with respect to *Escherichia coli* K-12 (Mandel, M. and Higa, A., J. Mol. Biol., 53, 159 (1970)) or the method of effecting the introduction in the propagation state (so-called competent cell), thereby enabling the cell to incorporate DNA, as reported with respect to *Bacillus subtilis* (Ducan, C. H., Wilson, G. A., and Young, F. E., Gene, 1, 153 (1977)). Alternately, the introduction of plasmid into the DNA-receiving bacterium can be effected by transforming the DNA-receiving bacterium into protoplast or spheroplast capable of easily incorporating DNA, as well known with respect to *Bacillus subtilis*, Actinomycetes, and yeasts (Chang, S. and Choen, S. N., Molec. Gen. Genet., 168, 111 (1979); Bibb, M. J., Ward, J. M., and Hopwood, O. A., Nature, 274, 398 (1970); Hinnen, A., Hicks, J. B., and Fink, G. R., Proc. Natl. Acad. Sci. USA, 75, 1929 (1978)).

In the case of the protoplast method, ample high frequency can be obtained even by the aforementioned method using *Bacillus subtilis*. Naturally, the method of effecting incorporation of DNA into a protoplast of genus Corynebacterium or genus Brevibacterium in the presence of polyethylene glycol or polyvinyl alcohol and a divalent metal ion as disclosed in Japanese Laid-open Patent Application 57-183799 can be utilized. The same effect can be obtained by the method of promoting the incorporation of DNA by the addition of carboxymethyl cellulose, dextran, Phycol, or Pluronic F68 (made by Serva Co.) in the place of polyethylene glycol or polyvinyl alcohol.

Selection of a strain retaining a recombinant plasmid capable of transduction is effected by the following method. Given strains are subjected to transformation and then allowed to form colonies on a suitable culture medium. The colonies are mixed. The mixture is subjected to bacteriolysis with a phage to prepare a phage solution. This phage solution is caused to infect a new host strain. Then the infected host is analyzed to screen out strains which have incorporated plasmids. When a gene controlling resistance to a chemical is present on such plasmids, this particular character can be selectively utilized. Thus, a strain retaining the desired plasmid can be easily obtained.

Desired isolation of the plasmid DNA from the strain retaining the recombinant plasmid is accomplished by causing bacteriolysis of the cell, as by the lysozyme-SDS treatment, treating the resulting bacteriolysis product with phenol, adding to the solution ethanol of a volume twice as large thereby inducing precipitation of DNA, and recovering the precipitated DNA.

The invention now being generally described, the same will be better understood by reference to the following specific examples which are intended for purposes of illustration only and are not to be considered limiting of the invention unless otherwise specified.

EXAMPLE 1

(1) Preparation of $F_1$ phage DNA

A phage $F_1$ used for the production of a composite plasmid was prepared by using *Brevibacterium lactofermentum* ATCC 13869 as a host bacterium.

The $F_1$ phage DNA was prepared by the following procedure. A strain of *Brevibacterium lactofermentum* ATCC 13869 was inoculated in 1 liter of CMG medium (containing 1 g of peptone, 1 g of yeast extract, 0.5 g of glucose, and 0.5 g of NaCl each per dl and adjusted to pH 7.2) and shaken at 30° C. for about one hour for culture and, with $F_1$ phage added thereto in an amount calculated to give multiplicity of infection (moi) of about 0.1, shaken continuously for 5 hours to induce bacteriolysis with the phage. The resultant bacteriolyzate was filtered through a high-flow super cell (made by Junsei Kagaku) to remove the residual cells. The filtrate and deoxyribonuclease I and ribonuclease A (made by Sigma Co.) each added in an amount of 10 μg/ml thereto were left standing at 30° C. for 20 minutes. Further, the filtrate and pancreatin added in an amount of 200 μg/ml thereto were retained at 30° C. for 20 minutes. Then, the filtrate, with sodium chloride added thereto in an overall concentration of 0.5M and polyethylene glycol 6000 in an overall concentration of 10%, was left standing at 4° C. for one day to induce precipitation of the $F_1$ phage particles. The precipitate was recovered by centrifugation at 5000 rpm for ten minutes and dissolved in 10 ml of a TEN buffer (20 mM tris hydrochloride and 1 mM EDTA (pH 8.0)) containing 1% of SDS. From the resultant solution, the $F_1$ phage DNA was extracted by the ordinary phenol treatment. The extract was refined to afford finally about 5 mg of DNA.

Phage $F_1$ has been deposited with the American Type Culture Collection, 12301 Parklawn Drive, Rockville, Md. 20852, where it has been given the identifying number ATCC 40173.

(2) Preparation of DNA fragment containing $F_1$ phage cohesive end (COS)

In a buffer solution containing about 5 μg of $F_1$ phage DNA, a restriction endonuclease Hind III was left standing at 37° C. for 2 hours to effect perfect severance of the DNA chain. Part of the resulting reaction solution was heated at 70° C. for 10 minutes and then suddenly cooled. The reaction solution so treated and the remainder of the reaction solution not treated were collectively subjected to electrophoresis in 0.8% agarose gel. As the result of this electrophoresis, it was found that the portion, about 2.1 kb, of the $F_1$ 1 phage DNA fragment produced by the Hind III treatment was separated into two fragments, about 1.6 kb and about 0.5 kb, and that a cohesive end (COS) was present in the 2.1 kb fragment. This 2.1 kb fragment was extracted from the agarose gel and then refined, to afford about 0.4 μg of DNA.

(3) Preparation of plasmid DNA

As a vector pAJ 43 (deposited under the designation of AJ 11997, FERM-P6857; molecular weight 3.4 megadaltons) was used.

From pAJ 655 (Japanese Laid-open Patent Application 58-1192900), which has been deposited as *Corynebacterium glutamicum* SR8201 ATCC 39135, pAJ 43 was produced as follows:

*Brevibacterium lactofermentum* No. 64 retaining pAJ 655 failed to grow on a CMG agar medium (containing 10 g of peptone, 10 g of yeast extract, 5 g of glucose, 5 g of NaCl, and 20 g of agar per liter and adjusted to pH 7.2) containing chloramphenicol in an amount of 100 μg/ml. One strain resistant to chloramphenicol at a concentration of 100 μg/ml was obtained by culturing the bacterium on the CMG medium, then culturing it overnight at 30° C. on a CMG liquid medium containing chloramphenicol in an amount of 100 μg/ml, and subjecting the cultured bacterium to one to two days culture at 30° C. as applied on a CMG medium containing chloramphenicol at the same concentration. When this strain was tested on a CMG medium for its resistance to chloramphenicol, it was found to resist the compound up to the concentration of 200 μg/ml.

From the strain resistant to chloramphenicol of high concentration as described above, pAJ 43 DNA was prepared as follows. First, this strain was inoculated to 1 liter of CMG liquid medium containing chloramphenicol in an amount of 10 μg/ml and cultured at 30° C. until the latter part of the logarithmic growth phase. The cells consequently produced were collected. The mass of cells was subjected to bacteriolysis with lysozyme and SDS by ordinary methods. The resulting bacteriolyzate was supercentrifuged at 30,000×g for 30 minutes to produce a supernatant. The supernatant was combined with polyethylene glycol (in an overall concentration of 10%) to induce precipitation of DNA. The mixture was concentrated. The precipitate was dissolved in 10 ml of a Tris-EDTA-NaCl (TEN) buffer (pH 8.0). The DNA was treated with ribonuclease I (used in a concentration of 50 μg/ml) at 37° C. for 30 minutes. It was then extracted from phenol. The extracted DN was left standing at −20° C. to induce precipitation of DNA in ethanol of a volume twice as large. The precipitate was dissolved in 1 ml of Tris-EDTA-NaCl buffer. By subjecting this DNA solution to agarose gel electrophoresis (voltage 5 V per 1 cm of gel for 15 hours), pure pAJ 43 plasmid DNA was obtained fractionally in an overall amount of 150 μg.

The molecular weight of pAJ 43 was determined by agarose-gel electrophoresis. This agarose-gel electrophoresis was carried out in a 0.8% gel under a fixed voltage of 5 V per cm of gel length for 15 hours in accordance with the method proposed by P. A. Sharp et al. (Biochemistry, 12, 3055 (1973)). The molecular weight was determined by causing 0.5 unit of a restriction enzyme, Hind III, capable of severing pAJ 43 at one point, to react upon 0.5 μg of pAJ 43 at 37° C. for one hours, straightening the severed pAJ 43, and comparing it with a molecular weight marker of known molecular weight, Hind III fragments of λ phage (purchased from BRL), in terms of mobility. Thus, the molecular weight was calculated to be 3.4 Md.

The DNA fragment so obtained with the restriction enzyme was analyzed by agarose-gel electrophoresis. The results indicate that pAJ 43 was a miniplasmid containing an approximately 1-Md fragment containing the chloramphenicol-resistant gene region of pBR 325 produced in vivo by deletion from pAJ 655 and an approximately 2.4-Md fragment containing a region essential for the maintenance of the replication of pAM 330.

(4) Insertion of DNA fragment containing the COS of $F_1$ phage into vector

About 1 μg of the plasmid pAJ 43 obtained in (3) above was contacted with the restriction endonuclease Hind III at 37° C. for two hours to effect perfect severance. The pAJ 43 fragment so produced was heated at 65° C. for 10 minutes. The treated pAJ 43 fragment and 2.1 kb of the DNA fragment obtained in (2) above added thereto were caused to react with DNA ligase originating from $T_4$ phage at 10° C. for 24 hours in the presence of ATP and dithiothreitol to effect linkage of the DNA chain. By adding ethanol of a volume twice as large to the resulting reaction mixture, the DNA linked by the reaction was precipitated and collected.

The DNA so obtained was dissolved in a small amount of TEN buffer and used for the following transformation.

(5) Transformation

The transformation was carried out by the protoplast transformation method. The Brevibacterium lactofermentum AJ12036, FERM-BP 734 (FERM-P 7559) used as a recipient bacterium was separated in the form of a streptomycin-resistant strain from the strain of Brevibacterium lactofermentum ATCC 13869. First the recipient bacterium was cultured in 5 ml of a CMG liquid medium until the initial stage of the logarithmic growth phase and, with penicillin added thereto in a concentration of 0.6 unit/ml, subjected further to 1.5-hour shaken culture. The cells grown consequently in the culture medium were collected by centrifugation. The cells were cleaned with 0.5 ml of a SMMP medium (pH 6.5) consisting of 0.5 M sucrose, 20 mM maleic acid, 20 mM magnesium chloride, and 3.5% of Penassay broth (Difco). They were then left suspended in a SMMP medium containing lysozyme in a concentration of 10 mg/ml at 30° C. for 20 hours to effect conversion into protoplasts. The protoplasts produced were separated by a 10-minute centrifugation at 6000×g, cleaned with SMMP, and suspended again in 0.5 ml of SMMP. The protoplast so produced and about 1 μg of DNA prepared in (4) above were mixed in the presence of 5 mM of EDTA. The resultant mixture, with polyethylene glycol added thereto in an overall concentration of 30%, was left standing at room temperature for two minutes to effect incorporation of the DNA into the protoplast. The protoplast was cleaned with 1 ml of the SMMP medium, suspended again in 1 ml of SMMP medium, and cultured therein at 30° for two hours for phenotypic expression. The resulting culture broth was applied on the protoplast regeneration medium at pH 7.0. The protoplast regeneration medium contained 12 g of tris(hydroxymethyl)aminomethane, 0.5 g of KCl, 10 g of glucose, 8.1 g of $MgCl_2.6H_2O$, 2.2 g of $CaCl,.2H_2O$, 4 g of peptone, 4 g of powdered yeast extract, 1 g of casamino acid, 0.2 g of $K_2HPO_4$, 135 g of sodium succinate, and 8 g of agar per liter and 3 μg/ml of chloramphenicol.

After 10-days culture at 30° C., about 1,000 chloramphenicol-resistant colonies were formed.

(6) Transduction

All the colonies grown as described above (5) were scraped off and suspended in physiological salt water. Part of the suspension and about $10^5$ of $F_1$ phage were spread on one plate of CMG medium containing 2% of agar and 10 μg of chloramphenicol per ml and cultured at 30° C. for one day. When the phenomenon of bacteriolysis by the $F_1$ phage was observed on the plate medium, 5 ml of physiological salt water was added to the plate medium to suspend the phage particles. The suspension was centrifuged at 15000 rpm for 10 minutes to remove residual cells and then passed through a bacterial filter (pore size 0.22 μ) to remove live cells.

About $10^9$ cells of Brevibacterium lactofermentum AJ 12036 in the logarithmic growth phase and 0.1 ml of the aforementioned phage solution added thereto were gently shaken at 30° C. for 90 minutes. The shaken mixture was centrifuged at 3000 rpm for 10 minutes to recover cells. The cells were washed twice with physiological salt solution. The cleaned cells were applied to a CMG medium plate containing 2% of agar and chloramphenicol in an amount of 10 μg/ml. After two-days culture at 30° C., three colonies were produced. These three strains were each suspended in physiological salt solution and cultured in conjunction with $F_1$ phage on a plate agar medium as described above to prepare a phage solution to effect transduction to the AJ 12036 strain.

No transducing property was detected in the phage solution obtained from the strain retaining pAJ 43, but occurrence of a chloramphenicol-resistant colony was observed in high frequency in the phage solution obtained from each of the aforementioned three strains. About $10^3$ chloramphenicol-resistant colonies occurred when about $10^9$ of the strain of recipient bacterium AJ 12036 was infected with about $10^7$ phage particles obtained from AJ 12136, FERM-BP 735 (FERM-P 7560) (Fermentation Research Institute, Ibaragi-ken, Japan), one of the three strains. In the resistant colonies and the strain of AJ 12136, about 4.8 Md of plasmid was detected. This plasmid was clearly identified to be a cosmid consisting of pAJ 43 (3.4 Md) of vector and a DNA fragment (1.4 Md) containing the COS region of $F_1$ phage and possessing the property of transduction. The cosmid found in the strain of AJ 12136 was designated as pAJ 667.

The phage solution derived from AJ 12136 was used to effect introduction of pAJ 667 into the strain of Cory-

*nebacterium glutamicum* ATCC 13060. When about $10^9$ phage articles were used, there were obtained 49 chloramphenicol-resistant strains. In each of these strains, 4.8 megadaltons of pAJ 667 plasmid DNA were detected. The results clearly indicate that the introduction of pAJ 667 into the strain of *Corynebacterium glutamicum* ATCC 13060 was accomplished by transduction.

Separately, a plasmid pAJ 668 capable of transduction could be similarly obtained by using pAJ 1844 (Japanese Laid-open Patent Application 58-192900) which has been deposited as *Corynebacterium glutamicum* SR 8202 ATCC 39136 as the plasmid vector and CP-23 phage (J. Gen. Appl. Microbiol., 22, 119 (1976) as the phage.

EXAMPLE 2

(1) Preparation of DNA fragment containing Kanamycin-resistant gene originating in pUC4K With restriction endonuclease Bam HI, 5 μg of pUC4K [product of Farmacia; Gene, 19, 259 (1982)] was maintained at 37° C. for two hours to effect complete cleavage. Then it was subjected to electrophoresis in a 5% agarose gel. The results of the electrophoresis clearly indicate the presence of a kanamycin-resistant gene in the fragment, abut 1.3 kb, produced by the treatment with Bam HI. This 1.3-kb fragment was purified by extraction from agarose gel, to obtained about 0.5 μg of DNA.

(2) Insertion of DNA fragment containing kanamycin-resistant gene into cosmid pAJ667

About 1 μg of the cosmid pAJ667 prepared by the procedure described in (3) of Example 1 was maintained with restriction endonuclease Bam HI at 37° C. for two hours to effect complete cleavage. The cleaved cosmid was treated at 65° C. for ten minutes and combined with 1.3 kb of the DNA fragment obtained in (1) above. The mixture was treated with a DNA ligase originating in the $T_4$ phage at 10° C. for 24 hours in the presence of ATP and dithiothreitol to effect reunion of the DNA chain. The reunion reaction was terminated by addition to the reaction solution of ethanol of a volume twice as large. The DNA in the reaction mixture was precipitated and collected.

The DNA so obtained was dissolved in a small amount of TEN buffer and subjected to transformation as described below.

(3) Transformation

The DNA solution was transformed by the protoplast transformation method. The recipient, *Brevibacterium lactofermentum* AJ 12036 (FERM-P 7559), was isolated as a streptomycin-resistant strain from the strain of *Brevibacterium lactofermentum* ATCC 13869. First, this recipient was cultured on 5 ml of CMB solution culture medium until the initial stage of the logarithmic growth phase. The grown recipient, with penicillin G added to the culture medium in a concentration of 0.6 unit/ml, was shake-cultured for 1.5 hours. The resultant culture broth was centrifuged to collect cells. The cells were cleaned with 0.5 ml of SMMP culture medium (pH 6.5) containing 0.5 M sucrose, 20 mM maleic acid, 20 mM magnesium chloride, and 3.5% Penassay broth (Difco). Then, the cleaned cells were suspended in SMMP culture medium containing 10 mg of lysozyme per ml and held at 30° C. for 20 hours to undergo conversion into protoplasts. They were separated by centrifuging the culture medium at 6000×g for ten minutes and again suspended in 0.5 ml of SMMP culture medium. The protoplasts so obtained were mixed with about 1 μg of the DNA prepared in (2) above in a preparation of 5 mM of EDTA. The resulting mixture and polyethylene glycol added thereto in a final concentration of 30% were left standing at room temperature for two minutes to effect incorporation of DNA into the protoplast. The protoplast was cleaned with 1 ml of SMMP culture medium, then suspended again in 1 ml of SMMP culture medium, and cultured at 30° C. for two hours. The resultant culture broth was applied on the protoplast reculture medium of pH 7.0. This protoplast reculture medium contained 12 g of tris(hydroxymethyl)aminomethane, 0.5 g of KCl, 10 g of glucose, 8.1 g of $MgCl_2.6H_2O$, 2.2 g of $CaCl_2.H_2O$, 4 g of peptone, 4 g of powdered yeast extract, 1 g of casamino acid (Difco), 0.2 g of $K_2HPO_4$, 135 g of sodium succinate, 8 g of agar, and 100 μg/ml of kanamycin per liter of distilled water.

After six-days culture at 30° C., about 30 kanamycin-resistant colonies appeared on the culture medium. In one strain, AJ 12173, FERM-BP 743 (FERM P-7885, isolated from the colonies and cultured on CMG agar culture medium containing kanamycin in a concentration of 25 μg/ml (containing 10 g of peptone, 10 g of yeast extract, 5 g of glucose, 5 g of NaCl, and 20 g of agar per liter and adjusted to pH 7.2), about 5.7 Md of plasmid was detected. The fact that this plasmid was formed from pAJ 667 vector (4.8 Md) and 0.9 Md of a DNA fragment containing kanamycin-resistant gene originating in pUC4K was confirmed by causing the plasmid to undergo reaction with the restriction endonuclease Bam HI at 37° C. for two hours and comparing the mobility thereof with that of a molecular weight marker of known molecular weight, Hind III fragment of λ phage (purchased from BRL). The plasmid detected from the strain AJ 12173 has been designated as pAJ670. The restriction enzyme map of pAJ670 is illustrated in the FIGURE.

(4) Transduction

About $10^8$ cells of AJ 12173 retaining pAJ670 in the logarithmic growth phase and about $10^5$ of $F_l$ phage were spread on one CMG plate culture medium containing 2% of agar and 25 μg/ml of kanamycin and cultured at 30° C. for one day. As the phenomenon of bacteriolysis by the $F_1$ phage was recognized on the plate medium, 5 ml of physiological salt solution was added to the plate medium to suspend phage particles. The suspension was centrifuged at 1500 rpm for ten minutes to remove residual cells, and the residue of the centrifugation was passed through a filter for cell removal (pore size 0.22 μ) to remove live cells.

About $10^9$ cells of *Brevibacterium lactofermentum* AJ 12036 in the logarithmic growth phase and 0.1 ml ($10^6$ pfu) of the aforementioned phage suspension added thereto were gently shaken at 30° C. for 90 minutes. The resulting mixture was centrifuged at 3000 rpm for ten minutes to recover cells. The cells were washed twice with physiological salt solution. The cleaned cells were applied to a CMG plate medium containing 2% of agar and 25 μg/ml of kanamycin. Two-days culture at 30° C. resulted in production of about $10^3$ kanamycin-resistant colonies. In these resistant colonies, about 5.7 Md of plasmid pAJ670 was detected, clearly indicating that the transduction resulted in successful introduction of pAJ670 into the AJ 12036 strain. The frequency of the pAJ670 transduction was on the same order as pAJ667.

The F₁ phage used in this embodiment of the invention was lysogenized in the AJ 12173 strain and was released into the culture medium either through spontaneous induction or through shaken culture in the liquid CMG culture medium containing 0.05 to 0.2 μg/ml of mitomycin C. Phage particles are obtained easily in a high yield by causing the F₁ phage to infect a strain of *Brevibacterium lactofermentum* ATCC 13869.

The plasmid pAJ43 has been deposited as *Brevibacterium lactofermentum* AJ 11997, FERM-P 6857, but can also be easily obtained from pAJ 667 or pAJ 670 by cleaving them with Hind III.

The invention now being described, it will be apparent to those of ordinary skill in the art that many changes and modifications can be made thereto without departing from the spirit or scope of the invention as set forth herein.

What is claimed as new and desired to be secured by Letters Patent of the United States is:

1. A composite vector capable of transducing a Coryneform bacterium, wherein said composite vector comprises a first DNA segment containing genetic information for replication of a plasmid capable of propagating in a Coryneform bacterium and a second DNA segment containing a DNA region of a phage capable of propagating in said bacterium, wherein said DNA region is a region incorporated into a particle of said phage when said bacterium is infected with said phage.

2. The vector of claim 1, wherein said vector is a plasmid.

3. The vector of claim 2, wherein said DNA region comprises a cohesive end.

4. The vector of claim 1, wherein said second DNA segment comprises an entire phage DNA.

5. The composite vector of claim 1, wherein said first DNA segment comprises an entire plasmid.

6. The composite vector of claim 1, wherein said vector is pAJ 667 or pAJ 667 having inserted therein an endogenous DNA segment.

7. The composite vector of claim 1, wherein said vector is pAJ 668 or pAJ 668 having inserted therein endogenous DNA.

8. The composite vector of claim 1, wherein said vector is pAJ 670 or pAJ 670 having inserted therein endogenous DNA.

9. A Coryneform bacterium containing the composite vector of claim 1.

10. The composite vector of claim 1, wherein said second DNA segment comprises a restriction fragment of phage DNA.

11. The composite vector of claim 1, wherein said first DNA segment comprises a restriction fragment of plasmid DNA.

* * * * *